United States Patent [19]
Kojima et al.

[11] Patent Number: 5,872,009
[45] Date of Patent: Feb. 16, 1999

[54] METHOD FOR MEASURING BILIRUBIN

[75] Inventors: Ryo Kojima; Katsuhiro Katayama; Yoshikiyo Sasagawa, all of Koriyama, Japan

[73] Assignee: Nitto Boseki Co., Ltd., Fukushima, Japan

[21] Appl. No.: 849,080

[22] PCT Filed: Nov. 30, 1995

[86] PCT No.: PCT/JP95/02445

§ 371 Date: Jun. 30, 1997

§ 102(e) Date: Jun. 30, 1997

[87] PCT Pub. No.: WO96/17251

PCT Pub. Date: Jun. 6, 1996

[30] Foreign Application Priority Data

Dec. 2, 1994 [JP] Japan .................................... 6-324032

[51] Int. Cl.$^6$ .................................................. G01N 33/00
[52] U.S. Cl. ........................... 436/97; 436/110; 436/164; 436/174; 436/175; 422/61
[58] Field of Search ................................. 436/12, 63, 97, 436/106, 110, 164, 174, 175; 422/61

[56] References Cited

U.S. PATENT DOCUMENTS

| | | | |
|---|---|---|---|
| 4,404,286 | 9/1983 | Shull | 436/97 |
| 4,672,041 | 6/1987 | Jain | 436/97 |
| 5,104,794 | 4/1992 | Kondo et al. | 435/25 |
| 5,149,272 | 9/1992 | Wu et al. | 436/97 |
| 5,250,441 | 10/1993 | Vogt et al. | 436/111 |
| 5,294,403 | 3/1994 | Meiattini | 422/61 |
| 5,449,623 | 9/1995 | Tokuda et al. | 436/97 |

FOREIGN PATENT DOCUMENTS

| | | |
|---|---|---|
| 0 217 197 | 4/1987 | European Pat. Off. . |
| 0484 133 | 5/1992 | European Pat. Off. . |
| 59-166862 | 9/1984 | Japan . |
| 60-040957 | 3/1985 | Japan . |
| 60-178361 | 9/1985 | Japan . |
| 62-75349 | 4/1987 | Japan . |
| 02203271 | 8/1990 | Japan . |
| 2-203271 | 8/1990 | Japan . |
| 5-18978 | 1/1993 | Japan . |
| 8303254 | 9/1983 | WIPO . |

OTHER PUBLICATIONS

Suzuki et al. "Comparison of stability . . . and serum bilirubins", *Seibutsu Shiryo Bunseki*, vol. 17(5) pp. 323–327 1994.

*Primary Examiner*—Maureen M. Wallenhorst
*Attorney, Agent, or Firm*—Armstrong, Westerman, Hattori, McLeland & Naughton

[57] ABSTRACT

Total bilirubin or direct bilirubin is measured by allowing nitrous acid as an oxidizing agent to act on a sample of living body fluid, and measuring optical changes of the sample. For measuring the direct bilirubin, nitrous acid is allowed to act on the sample in the presence of thiourea as a reaction inhibitor for indirect bilirubin. For measuring the total bilirubin, nitrous acid is allowed to act on the sample in the presence of cetyltrimethylammonium bromide as a reaction accelerator. Or, direct bilirubin is measured by allowing an oxidizing agent to act on a sample of living body fluid in the presence of a specific non-ionic surfactant. These methods have a good correlation to the conventional enzymatic method and a good reagent stability and provide safe methods for measuring bilirubin with less danger to environmental pollution.

11 Claims, 5 Drawing Sheets

FIG.1

| | ANALYSIS | CALI-BRATION | RANGE | STD CON-CENTRATION |
|---|---|---|---|---|
| ANALYTICAL PROCEDURE/ MEASUREMENT POINT | 2-POINT END [A] 10 [A] 16 | 34 | 0 | 0 |
| WAVELENGTH (SUB/MAIN) | [A] 450 [A] | | | |
| SAMPLE VOLUME (STANDARD) | 6.0 | 0.0 | 0 | |
| SAMPLE VOLUME (DECREASED) | 4.0 | 0.0 | 0 | |
| SAMPLE VOLUME (INCREASED) | 8.0 | 0.0 | 0 | |
| DILUTING SOLUTION | WATER | 0 | | |
| REAGENT VOLUME ADDED (R1) | 180 | 0 | 00303 | 0 |
| REAGENT VOLUME ADDED (R2) | 0 | 0 | 00303 | 0 |
| REAGENT VOLUME ADDED (R3) | 45 | 0 | 00303 | 0 |
| REAGENT VOLUME ADDED (R4) | 0 | 0 | 00303 | 0 |
| REACTION LIMIT ABSORBANCY | 0 | DECREASE [A] | BIPHASIC ASSAY | [A] |
| PROZONE LIMIT VALUE | -32000 | 34 | LOWER LIMIT [A] | |
| CELL WASHING AGENT | WASHING AGENT 1 | [A] | | |

CONFIRMATION OF FREE FORM BILIRUBIN AND CONJUGATE FORM BILIRUBIN IN THE METHOD FOR MEASURING DIRECT BILIRUBIN ACCORDING TO THE PRESENT INVENTION

Y = 0.9961X + 0.0237
R = 0.99719

Y = 1.0131X + 0.1862
R = 0.99946

CONFIRMATION OF FREE FORM BILIRUBIN AND CONJUGATE FORM BILIRUBIN IN THE METHOD FOR MEASURING TOTAL BILIRUBIN ACCORDING TO THE PRESENT INVENTION

METHOD FOR MEASURING BILIRUBIN

TECHNICAL FIELD

The present invention relates to a method for measuring bilirubin contained in a living body fluid such as plasma, serum, urine, etc.

More particularly, the present invention relates to a method for measuring bilirubin, which comprises allowing nitrous acid as an oxidizing agent to act on a sample of living body fluid, thereby measuring optical changes of the sample, and also to a method for measuring direct bilirubin with a high sensitivity, which comprises allowing an oxidizing agent to act on a sample of living body fluid in the presence of a specific non-ionic surfactant, thereby measuring optical changes of the sample.

BACKGROUND ART

Bilirubin is a metabolic product of hemoglobin derived from aged erythrocyte and is the main component of bile pigment. Blood bilirubin includes direct bilirubin (conjugate form) and indirect bilirubin (free form). Direct bilirubin, whose propionic acid group on the side chain enzymatically forms an ester bond mainly with glucuronic acid in the liver, is highly water soluble, and reacts directly with a diazo reagent to form an azo coloring matter. Indirect bilirubin, whose propionic acid group is in a free state, is low in the water solubility and reacts with a diazo reagent only in the presence of a reaction accelerator such as alcohol, etc. to form an azo coloring matter.

Measurement values obtained by measuring bilirubin in blood includes a total bilirubin value and a direct bilirubin value. Total bilirubin value is a measurement value of conjugate form and free form in total, obtained by reaction with a diazo reagent in the presence of a reaction accelerator. Direct bilirubin value is a measurement value only of conjugate form, obtained by reaction with a diazo reagent in the absence of a reaction accelerator. Individual bilirubin concentrations of conjugate form and free form can be separately determined from these measurement values to make diagnosis of various liver diseases and diacrisis of jaundice. Thus, the measurement of bilirubin is an important phase of the clinical laboratory tests.

A diazo method for measuring color intensity of azobilirubin formed by the above-mentioned reaction of bilirubin with a diazo reagent is a conventional leading method for measuring bilirubin and has been widely used for diagnosis of various liver diseases.

Another method is to measure bilirubin on the basis of changes in absorbance of bilirubin by allowing an oxidizing agent to act on bilirubin in a sample of living body fluid to oxidize bilirubin. The method for measuring bilirubin, using such an oxidizing agent, includes, for example, a BOD method using bilirubin oxidaze (BOD) as an oxidizing agent, a chemical oxidation method using ferricyanide ions, copper ions, vanadate ions, etc. as an oxidizing agent in place of BOD, etc.

Other methods include, for example, a high performance liquid chromatographical method by high performance liquid chromatography, a film method using a mordant-coated film, etc.

Every one of these methods has both merits and demerits and has been not satisfactory yet.

That is, the diazo method has such problems that the reagent is unstable, that is, effective only about 5 days after the preparation and also ascorbic acid or hemoglobin present in a sample interferes with the measurement values. The BOD method has such problems that use of the enzyme inevitably increases measurement costs and the enzyme is effective only about 2 weeks after the preparation because the enzyme is difficult to be stabilized. The chemical oxidation method has such a disadvantage that use of highly toxic metal ions, etc. inevitably involves a waste water treatment problem and an environmental pollution problem. The high performance liquid chromatographic method or the film method needs a special measurement apparatus in spite of satisfactory measurement values, and has such a disadvantage as poor versatility in simultaneous multi-phasic measurement of a large number of samples like other phases of the clinical laboratory test chemistry.

In the current situation it is desirous to develop a method for measuring bilirubin, using a stable and safe reagent, which is applicable to versatile automatic analyzers and has a good correlation to the conventional method, particularly to the enzymatic method with distinguished characteristics.

DISCLOSURE OF THE INVENTION

The present invention has been established in view of the current situation and the object of the present invention is to provide a safe method for measuring bilirubin at a low cost with a good correlation to the conventional enzymatic method, a distinguished stability of a reagent, less interference of coexisting substances in a sample with measurement values, and less danger to environmental pollution.

Another object of the present invention is to provide a method for measuring bilirubin, which is capable of selectively measuring direct bilirubin with a high sensitivity.

As a result of extensive studies to attain these objects, the present inventor found such a surprising fact that direct bilirubin and total bilirubin can be quantitatively determined by using nitrous acid as an oxidizing agent and selecting reaction conditions such as addition of a reaction accelerator for accelerating oxidation of bilirubin by nitrous acid, particularly oxidation of indirect bilirubin or addition of a reaction inhibitor for inhibiting such an oxidation, etc.

As a result of further studies on the basis of such finding as above, the present inventor furthermore found that particularly direct bilirubin can be selectively determined with a high sensitivity by allowing nitrous acid as the oxidizing agent to act on a sample of living body fluid in the presence of a non-ionic surfactant selected from polyoxyethylene (n-alkyl or iso-alkyl) ethers having an HLB value of not less than 12 but less than 15 and polyoxyethylene (n-alkylphenyl) ethers having an HLB value of not less than 12 but not more than 19, and the method can be widely applied even to methods using other oxidizing agents than nitrous acid, and has established the present invention.

The present invention provides a method for measuring total bilirubin or direct bilirubin, which comprises allowing nitrous acid as an oxidizing agent to act on a sample of living body fluid and measuring optical changes of the sample.

Furthermore, the present invention provides a method for measuring direct bilirubin, which comprises allowing nitrous acid as an oxidizing agent to act on a sample of living body fluid in the presence of a reaction inhibitor for inhibiting oxidation of indirect bilirubin and measuring optical changes of the sample.

Still furthermore, the present invention provides a method for measuring total bilirubin, which comprises allowing nitrous acid as an oxidizing agent to act on a sample of living body fluid in the presence of a reaction accelerator for accelerating oxidation of indirect bilirubin and measuring optical changes of the sample.

Still furthermore, the present invention provides a kit for measuring bilirubin in a sample of living body fluid, which comprises i) an acidic solution and ii) a nitrite solution.

Still furthermore, the present invention provides a kit for measuring direct bilirubin in a sample of living body fluid, which comprises i) an acidic solution containing a reaction inhibitor and ii) a nitrite solution.

Still furthermore, the present invention provides a kit for measuring total bilirubin in a sample of living body fluid, which comprises i) an acidic solution containing a reaction accelerator and ii) a nitrite solution.

Still furthermore, the present invention provides a method for measuring direct bilirubin, which comprises allowing an oxidizing agent to act on a sample of living body fluid in the presence of at least one non-ionic surfactant selected from polyoxyethylene (n-alkyl or iso-alkyl)ethers having an HLB value of not less than 12 but less than 15 and polyoxyethylene (n-alkylphenyl)ethers having an HLB value of not less than 12 but not more than 19 and measuring optical changes of the sample.

Still furthermore, the present invention provides a kit for measuring direct bilirubin in a sample of living body fluid, which comprises i) an acidic solution containing at least one non-ionic surfactant selected from polyoxyethylene (n-alkyl or iso-alkyl)ethers having an HLB value of not less than 12 but less than 15 and polyoxyethylene (n-alkylphenyl)ethers having an HLB value of not less than 12 but not more than 19 and ii) an oxidizing agent solution.

BRIEF DESCRIPTION OF THE DRAWINGS

FIG. 1 shows specific conditions for carrying out the present method for measuring bilirubin in an automatic analyzer.

BEST MODE FOR CARRYING OUT THE INVENTION

Figure 2:
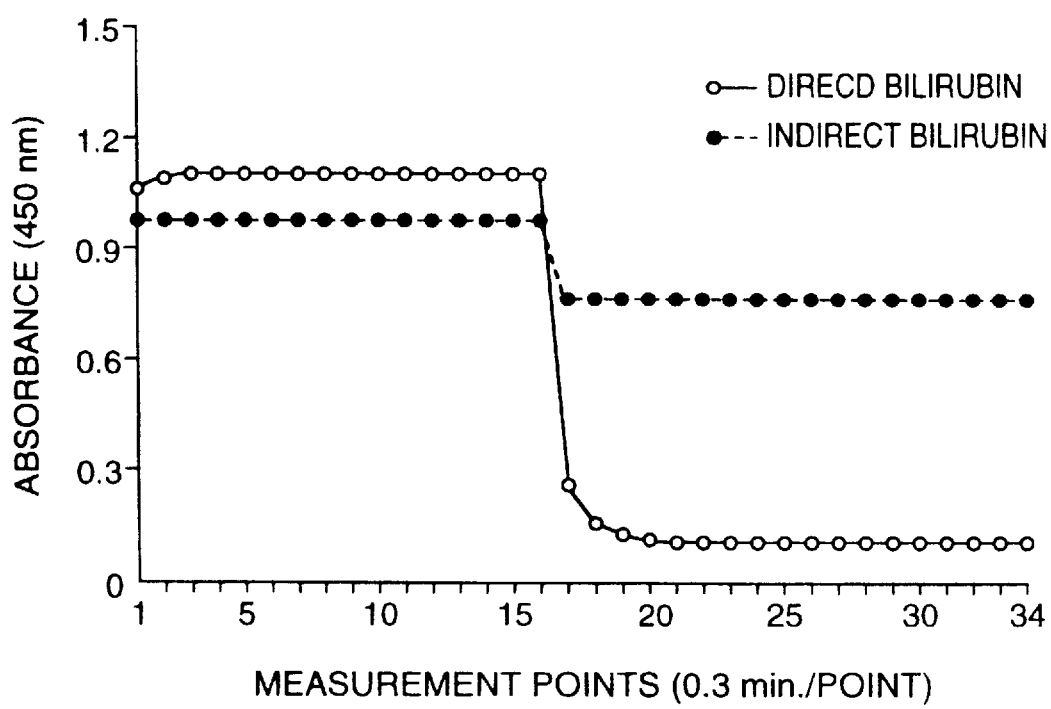
FIG. 2 shows results of measuring direct bilirubin or indirect bilirubin by the present nitrous acid oxidation method in the presence of thiourea as a reaction inhibitor, where changes in absorbance are observed with reaction time, and where measurement points (0.3 min./point) are given on the axis of abscissa and absorbance at 450 nm is given on the axis of ordinate.

In the present invention, total bilirubin or direct bilirubin is determined by allowing nitrous acid as an oxidizing agent to act on a sample of living body fluid and measuring optical changes of the sample. Such a determination can be carried out by using a kit for measuring bilrubin in living body fluid. A kit comprising an acidic solution and a nitrite solution is used for the determination.

In the present invention, a sample of living body fluid is a sample available from fluids from a living body and includes, for example, samples of plasma, serum, urine, etc.

In the present invention, action of nitrous acid as an oxidizing agent on a sample of living body fluid can be carried out usually by adding an acidic solution of citric acid, etc. to the sample of living body fluid and further adding thereto a nitrite solution. The acidic solution and the nitrite solution are usually aqueous solutions.

The acidic solution to be added to a sample of living body fluid contains an acid such as citric acid, lactic acid, acetic acid, phthalic acid, etc. and can preferably have a pH of 2 to 6, when joined with the nitrite solution.

A nitrite for use in preparation of a nitrite solution is not particularly limited, so long as it can be used to attain the object of the present invention, and is preferably an alkali metal salt. Sodium salt and potassium salt are particularly preferable because of their easy availability.

Concentration of nitrite for measuring bilirubin depends on an amount of a sample, but is not particularly limited, so long as it is a concentration capable of oxidizing bilirubin in the sample. A nitrite concentration in the ultimate reaction solution must be in a range of usually 0.01 to 20 mmol/l, preferably 0.05 to 4 mmol/l.

In the present method for measuring direct bilirubin, it is preferable to use a reaction inhibitor capable of being added to the reaction agent to prevent indirect bilirubin from oxidation by nitrous acid. The present method for measuring direct bilirubin can be carried out by using a kit for measuring direct bilirubin in a sample of living body fluid, which comprises an acidic solution containing a reaction inhibitor capable of inhibiting oxidation of indirect bilirubin and a nitrite solution.

Such a reaction inhibitor for the indirect biliruin for use in the present invention includes thiourea, thiourea having a lower alkyl at the N-position, a quaternary lower alkylammonium salt, an N-lower alkylpyridinium salt, a bipyridinium salt having a lower alkyl at the N-positions, etc. An alkyl having 1 to 6 carbon atoms is herein designated as a lower alkyl. In the present invention, a preferable lower alkyl is a straight chain lower alkyl because of their easy availability.

Preferable thiourea having a lower alkyl at the N-position includes 1,1,3,3-tetramethylthiourea, 1,1,3-trimethylthiourea, 1,3-dimethylthiourea and N-methylthiourea because of their easy availability.

Quaternary lower alkylammonium salt includes, for example, N-(lower alkyl)-N,N,N-trimethylammonium salt, N-(lower alkyl)-N,N,N-triethylammonium salt, and N-(lower alkyl)-N,N,N-tripropyl ammonium salt. Chlorides, bromides, etc. are preferable for these salts because of their easy availability.

Other reaction inhibitors includes, for example, hydrazines such as hydrazine, phenylhydrazine, salts thereof, etc.; hydroxylamines such as hydroxylamine, phenylhydroxylamine, salts thereof, etc.; oximes such as acetoxime, diacetylmonoxime, salicylaldoxime, etc.; aliphatic polyamines such as tetraethylenepentamine, triethylenetetramine, etc.; phenols such as phenol, p-chlorophenol, β-naphthol, etc., and so on.

These reaction inhibitors are effective even when alone, but in some cases the inhibition effect can be improved by combination of at least two thereof, and thus they may be used upon proper selection in view of the situations. The reaction of nitrous acid with direct bilirubin in the presence of a reaction inhibitor can be carried out usually by adding an acidic solution containing a reaction inhibitor to a sample of living body fluid and then adding thereto a nitrite solution. The acidic solution to be used for this purpose can be prepared by adding a reaction inhibitor to the abovementioned acidic solution, and the same nitrite solution as mentioned above can be used for this purpose.

In the reaction of nitrous acid with direct bilirubin in the presence of a reaction inhibitor, the reaction solution must be in a pH range of preferably 2 to 6, more preferably 3.5 to 4.5. At too high a pH the oxidation reaction will be hard to proceed, whereas at too low a pH the reaction-inhibiting effect on the indirect bilirubin will be lowered and accordingly the reaction selectivity will be lost.

Concentration of a reaction inhibitor to be used for this purpose is not particularly limited, so long as it is a concentration capable of inhibiting oxidation of free bilirubin in a sample, and is usually in a range of 0.01 to 10 w/v % as a concentration of ultimate reaction solution, though dependent on the kind of a reaction inhibitor.

In the present method for measuring total bilirubin, it is preferable to make a reaction accelerator capable of accelerating oxidation reaction of indirect bilirubin by an ordinary oxidizing agent, that is, the so called direct oxidizing agent, present in the reaction reagent, because the measurement time can be shortened. The present method for measuring total bilirubin can be carried out by using a kit comprising an acidic solution containing a reaction accelerator capable of accelerating oxidation of indirect bilirubin and a nitrite solution.

The reaction accelerator for use in the present invention is those usually used for this purpose in this field, and includes, for example, anionic surfactants such as sodium laurylsulfate, sodium laurylbenzenesulfonate, sodium cholate, etc.; cationic surfactants such as cetyltrimethylammonium bromide, cetylpyridinium chloride, etc.; amphoteric surfactants such as alkylbetaine, etc.; and so on. Above all, the cationic surfactants and amphoteric surfactants are preferable because of less interaction with protein under acidic conditions.

Reaction with direct bilirubin and indirect bilirubin in the presence of a reaction accelerator can be carried out by adding an acidic solution containing a reaction accelerator to a sample of living body fluid and then adding thereto a nitrite solution in the same manner as mentioned above. The reaction solution must be in a pH range of preferably 1.5 to 6, more preferably 2.5 to 4. At too high a pH the oxidation reaction will be retarded and a negative error will be liable to appear on the measurement value, whereas at too low a pH nonspecific reaction will be liable to take place and a positive error will be liable to appear on the measurement values.

Concentration of a reaction accelerator to be used for this purpose is not particularly limited, so long as it is a concentration capable of accelerating oxidation of bilirubin in a sample, and usually is in a range of 0.01 to 10 w/v %, preferably 0.1 to 5 w/v % as a concentration in the ultimate reaction solution.

Furthermore, the present invention provides a method for measuring direct bilirubin, which is capable of using other oxidizing agents than nitrous acid as an oxidizing agent, that is, a method for measuring direct bilirubin, which comprises allowing an oxidizing agent to act on a sample of living body fluid in the presence of at least one non-ionic surfactant selected from polyoxyethylene (n-alkyl or iso-alkyl)ethers having an HLB value of not less than 12 but less than 15 and polyoxyethylene (n-alkylphenyl)ethers having an HLB value of not less than 12 but not more than 19, and measuring optical changes of the sample.

In case of allowing an oxidizing agent to act on a sample of living body fluid in the presence of a specific non-ionic surfactant as mentioned above, the oxidizing agent will be liable to react with the direct bilirubin, whereas it will less liable to react with the indirect bilirubin, and accordingly selectivity to reaction of the oxidizing agent with the direct bilirubin will be improved. Furthermore, direct bilirubin can be exactly measured, even if a sample of living body fluid contains direct bilirubin at a high concentration.

The method for measuring the direct bilirubin can be carried out by using a kit comprising an acidic solution containing a specific non-ionic surfactant as mentioned above and an oxidizing agent solution.

Polyoxyethylene (n-alkyl or iso-alkyl)ethers having an HLB value of not less than 12 but less than 15 as one member of the specific non-ionic surfactant includes, for example, Adekatol SO-145 [trademark of polyoxyetylene (iso-alkyl)ether, made by Asahi Denka K.K], Adekatol SO-135 [trademark of polyoxyethylene (iso-alkyl)ether, made by Asahi Denka K.K.], Adekatol SO-120 [trademark of polyoxyethylene (iso-alkyl) ether, made by Asahi Denka K.K.], Emalgen 707 [trademark of polyoxyethylene (n-alkyl)ether, made by Kao K.K.], Emalgen 709 [trademark of polyoxyethylene (n-alkyl)-ether, made by Kao K.K.], etc. A non-ionic surfactant having an HLB value of less than 12 is not preferable, because its solution has a low cloudy point and will be liable to turn white turbid at the measurement temperature, that is, a temperature ranging from room temperature to 37° C. A non-ionic surfactant having an HLB value of not less than 15 is not preferable, because the absorbance of direct bilirubin in its solution will tend to be lowered, and thus no satisfactory color intensity will be obtained at the measurement and a negative error will be liable to appear on the measurement value of direct bilirubin. The HLB value is preferably in a range of 12 to 14.5, above all 12 to 14. Such a preferable non-ionic surfactant includes, for example, Adekatol SO-135, Emalgen 707, Adekatol SO-145, etc.

Another member of the non-ionic surfactants for use in the present invention is polyoxyethylene (n-alkylphenyl) ethers having an HLB value of not less than 12 but not more than 19, and includes, for example, Adekatol NP-675 [trademark of polyoxyethylene (n-nonylphenyl)ether, made by Asahi Denka K.K.], Adekatol NP-683 [trademark of polyoxyethylene (n-nonylphenyl) ether, made by Asahi Denka K.K.], Adekatol NP-690 [trademark of polyoxyethylene (n-nonylphenyl)ether, made by Asahi Denka K.K.], Adekatol NP-695 [trademark of polyoxyethylene (n-nonylphenyl)ether, made by Asahi Denka K.K.], Adekatol NP-700 [trademark of polyoxyethylene (n-nonylphenyl) ether, made by Asahi Denka K.K.), Adekatol NP-720 [trademark of polyoxyethylene (n-nonylphenyl)ether, made by Asahi Denka K.K.], etc. In case of these non-ionic surfactants, an HLB value of less than 12 is also not preferable for the same reason as mentioned above and an HLB value of more than 19 is also not preferable for the same reason as for the above-mentioned HLB value of not less than 15. A particularly preferable HLB value is in a range of 12 to 14.8, above all, 12 to 14.5, typical of which is Adekatol NP-695.

In the measurement of direct bilirubin in the presence of a specific non-ionic surfactant as mentioned above, the oxidizing agent will be less liable to react with the indirect bilirubin. For more selective measurement of direct bilirubin, it is preferable to use the same reaction inhibitor as mentioned above. Use of polyvinylpyrrolidone together with a reaction inhibitor will improve the reactivity of the oxidizing agent with the direct bilirubin, and thus it is particularly preferable to use polyvinylpyrrolidone in the measurement of direct bilirubin.

In the measurement of direct bilirubin by allowing an oxidizing agent to act on a sample of living body fluid in the presence of a specific surfactant as mentioned above, other oxidizing agents than nitrous acid can be used as an oxidizing agent. Such an oxidizing agent includes, for example, chemical oxidizing agents such as vanadate ions, trivalent manganese ions, divalent copper ions, etc. and enzymatic oxidizing agents such as bilirubin oxidase, etc.

Measurement of direct bilirubin in a sample of living body fluid in the presence of a specific non-ionic surfactant as mentioned above can be carried out by adding an acidic solution containing a non-ionic surfactant and, if required, a reaction inhibitor and polyvinylpyrrolidone to a sample of living body fluid and then adding thereto an oxidizing agent solution.

Concentration of an non-ionic surfactant to be used for this purpose must be in a range of usually 0.01 to 5%, preferably 0.1 to 1% as a concentration in the ultimate reaction solution. Concentration of a reaction inhibitor, when used, must be the same as in the above-mentioned method for measuring direct bilirubin. Concentration of polyvinylpyrrolidone, when used together with the reaction inhibitor, must be in a range of usually 0.01 to 5%, preferably 0.1 to 1% as a concentration of ultimate reaction solution.

Concentration of an oxidizing agent to be used for this purpose depends on the kind of the oxidizing agent, an amount of a sample of living body fluid, etc., and in case of chemical oxidizing agents such as vanadate ions, trivalent manganese ions, divalent cupper ions, etc., it must be in a range of usually 0.01 to 20 mM, preferably 0.04 to 4 mM, whereas in case of enzymatic oxidizing agents such as bilirubin oxidase, etc., it must be in a range of usually 0.1 to 20 KU/l, preferably 0.5 to 5 KU/l. In case of using nitrous acid as an oxidizing agent, nitrous acid can be used at the same concentration as mentioned above.

In the present method for measuring direct bilirubin or total bilirubin as mentioned above, other reagents such as a buffer species, antiseptics, a chelating agent, a surfactant, etc. can be used upon proper selection according to the well known procedure. These reagents can be used usually by addition thereof to the above-mentioned acidic solution.

For example, the presence of a chelating agent is preferable, because it lowers a reagent blank value to improve the precision of analysis, stabilizes the reagent solution and accelerates the oxidation of bilirubin. Preferable specific examples of the chelating agent to be used for this purpose are ethylenediaminetetracetic acid (EDTA), nitrilotriacetic acid (NTA), cyclohexanediaminetetraacetic acid (CyDTA), diethylenetriaminepentaacetic acid (DTPA), hydroxyethylethylenediaminetriacetic acid (EDTA-OH), triethylenetetraiminehexaacetic acid (TTHA), hydroxyethyliminodiacetic acid (HIDA), 1-hydroxyethane-1,1-diphosphonic acid, and alkali metal salts (e.g. lithium salts, sodium salts and potassium salts) thereof, ammonium salts thereof, etc. Concentrations of these chelating agents for use in the measurements of bilirubin are not particularly limited, so long as it is a concentration incapable of inhibiting the measurement of bilirubin. It must be in a range of usually 0.02 to 50 mM, preferably 0.1 to 30 mM, more preferably 1 to 20 mM as a concentration in the ultimate reaction solution.

The present method can be carried out, for example, in the following manner; for the measurement of total bilirubin concentration, an acidic solution containing a reaction accelerator as a first reagent is mixed with a sample of living body fluid containing bilirubin such as plasma, serum, urine, etc. and an absorbance in a wavelength range (430–460 nm) based on the bilirubin in the solution is measured to obtain the measurement value as "absorbance A". Then, a second reagent solution containing a nitrite is added to the solution to conduct oxidation reaction of bilirubin at 25° C. to 40° C. for 3 to 15 minutes, and then an absorbance in a wavelength range (430–460 nm) based on the bilirubin in the solution is again measured to obtain the measurement value as "absorbance B". The absorbance A and absorbance B thus obtained are corrected for the solution volume, etc. and a change in the absorbance before and after the oxidation reaction is determined. Total bilirubin concentration in the sample of living body fluid can be obtained from the change in absorbance thus determined and a working curve prepared in advance on the basis of charges in absorbance obtained in the same procedure as above, using standard solutions of known bilirubin concentrations.

For the measurement of direct bilirubin concentration, an acidic solution containing a reaction inhibitor in place of the reaction accelerator, or an acidic solution containing a specific non-ionic surfactant as mentioned above and, if required, a reaction inhibitor and polyvinylpyrrolidone is used as a first reagent and the same solution as used for above-mentioned measurement of total bilirubin concentration is used as a second reagent, followed by the same operations as for the measurement of total bilirubin concentration.

The present method is also applicable to versatile automatic analyzers commercially available for biochemical clinical tests. Specific examples of models of automatic analyzers for use in the present invention include Hitachi Model 7050, Hitachi Model 705, Hitachi Model 736, Hitachi Model 7150, Hitachi model 7170, Hitachi Model 7020, etc. though the present invention is not limited thereto. That is, any similar models can be used in the present invention.

Accordingly, total bilirubin value or direct bilirubin value in a large number of samples of living body fluid can be measured within a short time.

The present invention will be described in detail below, referring to Examples, which will never serve to limit the present invention.

EXAMPLE 1

Measurement of Direct Bilirubin by Nitrous Acid Oxidation Method Based on the Presence of Thiourea i) Object:

In case of measuring bilirubin by nitrous acid oxidation method, the following experiment was carried out to confirm that direct bilirubin can be selectively oxidized by adding thiourea as a reaction inhibitor thereto without oxidizing indirect bilirubin.

ii) Reagents used:
First Reagent
An aqueous solution containing the following components, adjusted to pH 4.0 by NaOH, was used as a first reagent (acidic solution):

| | |
|---|---|
| Citric acid monohydrate | 200 mM |
| Cyclohexanediaminetetraacetic acid (CyDTA) | 1 mM |
| Thiourea | 120 mM |
| Surfactant | 0.3% |

Second Reagent
An aqueous solution containing the following components was used as a second reagent (nitrite solution):

| | |
|---|---|
| Sodium nitrite | 5 mM |
| Sodium chloride | 150 mM |

Direct Bilirubin Standard
An aqueous solution containing ditaurobilirubin corresponding to 40 mg/dl of direct bilirubin was used as a direct bilirubin standard.

Indirect Bilirubin Standard
A 20 mM tris buffer solution containing free bilirubin corresponding to 40 mg/dl of indirect bilirubin was used as an indirect bilirubin standard.

iii) Procedure:
Measurement was carried out under conditions given in FIG. 1, using an automatic analyzer Hitachi Model 7170 (made by Hitachi, Ltd.). According to the conditions, 6 µl of bilirubin standard and 180 µl of first reagent were mixed together and the resulting liquid mixture was left standing at 37° C. for 5 minutes. Then, 45 µl of second reagent was added to the liquid mixture to initiate reaction. All these operations were carried out automatically by setting parameters. At every 0.3 minutes after the mixing of the bilirubin standard with the first reagent, absorbance (450 nm) of the liquid mixture was automatically measured. The results are shown in FIG. 2.

iv) Results:
As is evident from FIG. 2, a decrease in absorbance due to the solution volume dilution takes place by adding indirect bilirubin and sodium nitrate to the acidic solution in the presence of thiourea as a reaction inhibitor, but there is no change in absorbance based on indirect bilirubin. On the other hand, the absorbance based on direct bilirubin is selectively lowered under these conditions. That is, the indirect bilirubin cannot be oxidized, but only the direct bilirubin can be selectively oxidized under these conditions.

EXAMPLE 2
Correlation of Nitrous Acid Oxidation Method Based on the Presence of Thiourea to BOD Method in the Measurement of Direct Bilirubin i) Object:
To show whether or not the method based on the presence of thiourea can exactly measure direct bilirubin in a sample and investigate whether or not there is a correlation of the method to a BOD method as control.

ii) Measurement of direct bilirubin by the method based on the presence of thiourea:
The same first reagent and second reagent as in Example 1 were used. Nescoat BIL standard serum (containing 7.8 mg/dl of direct bilirubin and 12.1 mg/dl of total bilirubin), made by Nihon Shoji K.K., was used as a bilirubin standard serum for obtaining a working curve. Operations were carried out in the same procedure as in Example 1, except that fresh human serum was used in place of biliruin standards.

Figure 3:
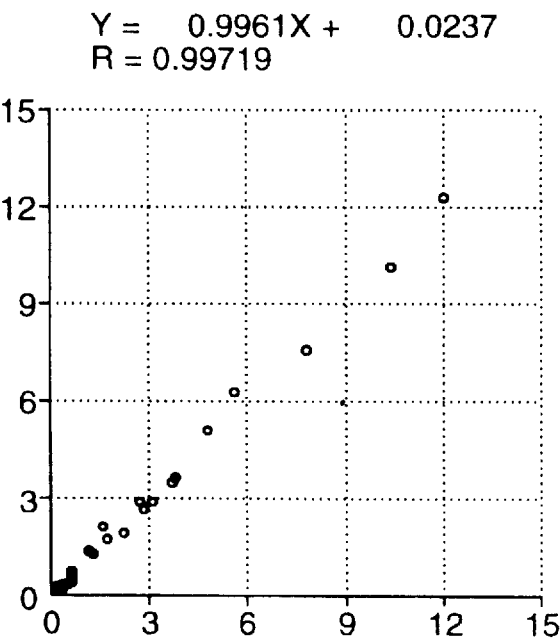
FIG. 3 shows correlation of the present nitrous acid oxidation method in the presence of thiourea to the BOD method in the measurement of direct bilirubin, where the direct bilirubin concentration (mg./dl) measured by the BOD method is given on the axis of abscissa and the direct bilirubin concentration (mg/dl) measured by the present nitrous acid oxidation method in the presence of thiourea is given on the axis of ordinate.

Concentration of direct bilirubin was determined in the following manner; the first reagent and fresh human serum were mixed together, and absorbance at 450 nm of the resulting solution mixture was measured to obtain the measurement value as "absorbance A". Then, the second reagent was added to the solution mixture to initiate oxidation reaction. Absorbance of the reaction solution was again measured to obtain the measurement value as "absorbance B". The value of absorbance A and absorbance B thus obtained were corrected for the solution volume and then a change in absorbance before and after the oxidation reaction was obtained. Concentration of direct bilirubin in the fresh human serum was determined from the change in absorbance thus obtained and a working curve prepared in advance on the basis of changes in absorbance obtained in the same manner as above, using standard solutions of known direct bilirubin concentrations.

iii) Measurement of direct bilirubin by BOD method:
Direct bilirubin was measured in a measurement kit for Nescoat D-BIL-VE (made by nihon Shoji K.K.) according to their manual.

iv) Correlation of nitrous acid method based on the presence of thiourea to BOD method:
Concentration of direct bilirubin in 44 samples of fresh human serum was measured by the method based on the presence of thiourea and the BOD method to investigate their correlation.

v) Results:
A graph of correlation results is shown in FIG. 3. The correlation coefficient was found to be 0.997 and the regression equation was found to be Y=0.996 X+0.023. It was found that there was a very good correlation therebetween, and concentration of direct bilirubin in human serum could be exactly measured according to the present invention.

EXAMPLE 3
Measurement of Total Bilirubin by Nitrous Acid Oxidation Method Based on the Presence of Cetyltrimethylammonium Bromide i) Object:
The following experiment was carried out to show that both indirect bilirubin and direct bilirubin can be oxidized by addition of cetyltrimethylammonium bromide as a reaction accelerator in the measurement of bilirubin by nitrous acid oxidation method, thereby enabling measurement of total bilirubin.

ii) Reagent used:
First Reagent:
An aqueous solution containing the following components, adjusted to pH 3.00 by NaOH, was used as a first reagent:

| | |
|---|---|
| Citric acid monohydrate | 200 mM |
| CyDTA | 1 mM |
| Cetyltrimethylammonium bromide | 1% |
| Surfactant | 0.3% |

Figure 4:
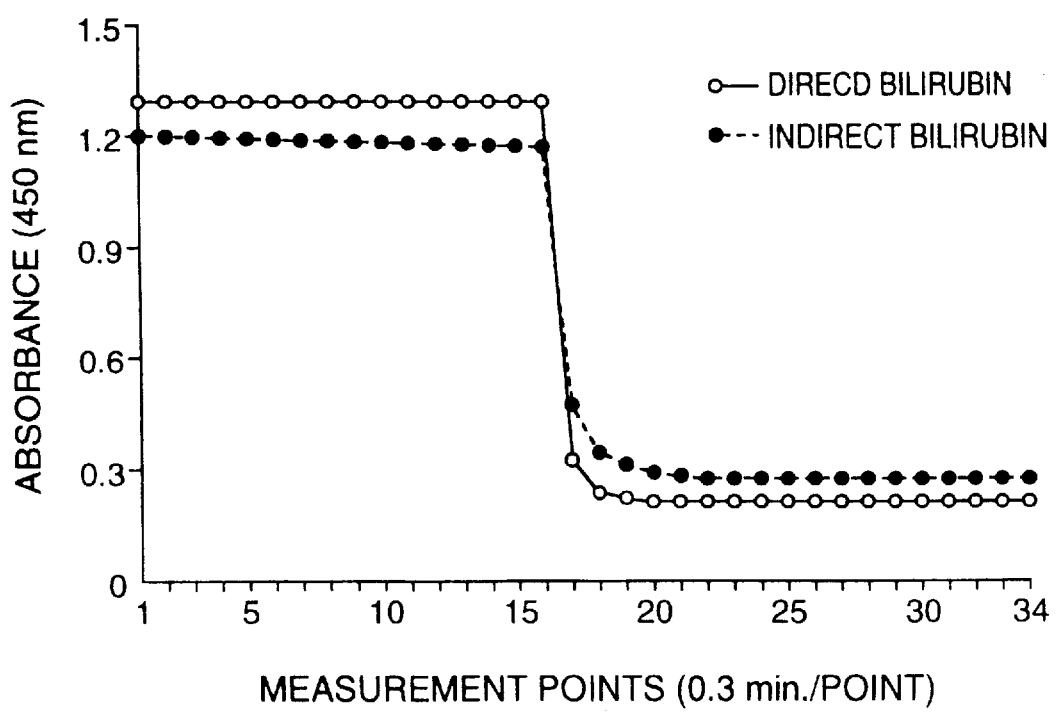
FIG. 4 shows results of measuring direct bilirubin or indirect bilirubin by the present nitrous acid oxidation method in the presence of cetyltrimethylammonium bromide as a reaction accelerator, where changes in absorbance are observed with time and where measurement points (0.3 min./point) are given on the axis of abscissa and absorbance at 450 nm is given on the axis of ordinate.

Second Reagent:
An aqueous solution containing the following components was used as a second reagent:

| | |
|---|---|
| Sodium nitrite | 5 mM |
| Sodium chloride | 150 mM | iii) Bilirubin standard:

The same direct bilirubin standard and indirect bilirubin standard as in Example 1 were used.

iv) Procedure:

Operations were carried out in the same manner as in Example 1. At every 0.3 minutes after the mixing of bilirubin standard with the first reagent, absorbance (450 nm) of the liquid mixture was automatically measured. The results are shown in FIG. 4.

v) Results:

In this Example, it is shown that the absorbance based on the indirect bilirubin disappear completely as well as the absorbance based on the direct bilirubin. That is, in this Example, it was found that the indirect bilirubin was completely oxidized as well as the direct bilirubin.

EXAMPLE 4

Correlation of the Nitrous Acid Oxidation Method Based on the Presence of Cetyltrimethylammonium Bromide to BOD Method in the Measurement of Total Bilirubin i) Object:

To show that the total bilirubin in a sample can be exactly measured by nitrous acid oxidation method based on the presence of cetyltrimethylammonium bromide and to investigate correlation of the method to BOD method as control.

ii) Measurement of total bilirubin by the method based on the presence of cetyltrimethylammonium bromide:

The same first reagent and second reagent as in Example 3 were used. Nescoat BIL standard serum (containing 7.8 mg/dl of direct bilirubin and 12.1 mg/dl of total bilirubin), made by Nihon Shoji K.K., was used as bilirubin standard serum for obtaining a working curve. Operations were carried out in the same procedure as in Example 3, except that fresh human serum was used in place of the bilirubin standards.

Figure 5:
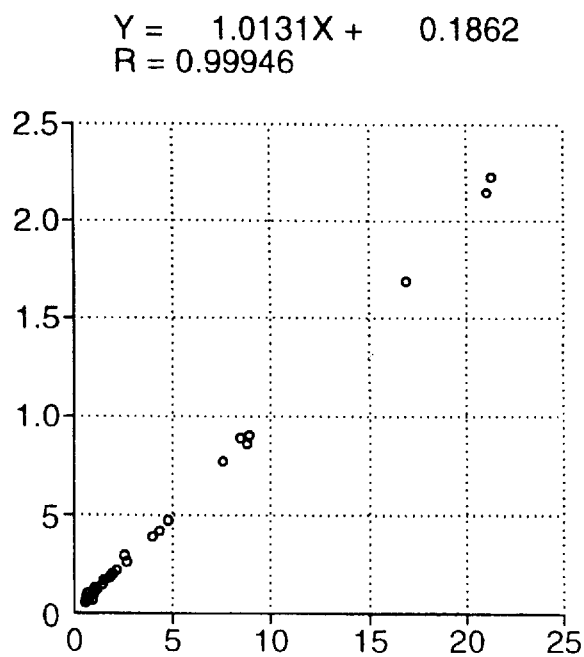
FIG. 5 shows correlation of the present nitrous acid oxidation method in the presence of cetyltrimethylammonium bromide to the BOD method in the measurement of total bilirubin, where total biluribin concentration (mg/dl) measured by the BOD method is given on the axis of abscissa and total bilirubin concentration (mg/dl) measured by the present nitrous acid oxidation method in the presence of cetyltrimethylammonium bromide is given on the axis of ordinate.

Concentration of total bilirubin was obtained in the following manner: the first reagent and the fresh human serum were mixed together and absorbance at 450 nm of the solution mixture was measured to obtain the measurement value as "absorbance A". Then, the second reagent was added to the solution mixture to initiate oxidation reaction and then the absorbance of the reaction solution was again measured to obtain the measurement value as "absorbance B". The values of absorbance A and absorbance B thus obtained were corrected for solution volume and then a change in absorbance before and after the oxidation reaction was obtained. Concentration of total bilirubin in the fresh human serum was determined from the change in absorbance thus obtained and a working curve prepared in advance on the basis of changes in absorbance obtained in the same manner as above, using standard solutions of known total bilirubin concentrations.

iii) Measurement of total bilirubin by BOD method:

Total bilirubin was measured in a measurement kit for Nescoat T-BIL-VE (made by Nihon Shoji K.K.) according to their manual.

iv) Correlation of nitrous acid oxidation method based on the presence of cetyltrimethylammonium bromide to BOD method:

Concentration of total bilirubin in 44 samples of fresh human serum was measured by the method based on the presence of cetyltrimethylammonium bromide and the BOD method to investigate their correlation.

v) Results:

A graph of correlation results is shown in FIG. 5. The correlation coefficient was found to be 0.999 and the regression equation was found to be Y=1.013 X+0.1862. It was found that there was a very good correlation therebetween, and concentration of total bilirubin in human serum could be exactly measured according to the present invention.

EXAMPLES 5 TO 13 AND COMPARATIVE EXAMPLES 1 TO 3

Measurement of Direct Bilirubin in the Presence and the Absence of a Non-Ionic Surfactant i) Object:

Direct bilirubin or indirect bilirubin was measured by adding to a sample a non-ionic surfactant selected from polyoxyethylene (n-alkyl or iso-alkyl)ethers having an HLB value of not less than 12 but less than 15 and polyoxyethylene (n-alkylphenyl)ethers having an HLB value of not less than 12 but not more than 19, and, if required, a reaction inhibitor for the indirect bilirubin and polyvinylpyrrolidone, allowing nitrous acid to act on the resulting liquid mixture and measuring optical changes at 450 nm of the sample. Similar experiments were carried out without such a non-ionic surfactant at the same time.

ii) Reagents used:

First Reagent:

An aqueous solution containing the following components, adjusted to pH 3.70 by NaOH, was used as a first reagent:

| | |
|---|---|
| Citric acid monohydrate | 100 mM |
| EDTA | 1 mM |

Components to be further contained in first reagent, as given in the following Table 1

Second Reagent:

An aqueous solution containing the following components was used as a second reagent:

| | |
|---|---|
| Sodium nitrite | 5 mM |
| Sodium chloride | 150 mM |

Sample:

For the measurement of direct bilirubin, a solution containing 10 mg/dl or 50 mg/dl of ditaurobilirubin was used. For the measurement of indirect bilirubin, a solution containing 50 mg/dl of indirect bilirubin was used. For the measurement of a sample of living body fluid, serum containing 2.3 mg/dl of direct bilirubin and 12.1 mg/dl of total bilirubin was used.

Working Curves:

Working curves were obtained by carrying out measurement according to the following procedure, using samples containing 10 mg/dl, 20 mg/dl, 30 mg/dl, 40 mg/dl and 50 mg/dl of ditaurobilirubin, respectively. Correlation coefficients of the working curves are shown in Table 1.

iii) Procedure:

Measurement was carried out under conditions given in Table 1, using an automatic analyzer Hitachi Model 7170 (made by Hitachi, Ltd.). According to the conditions, 6 μl of a sample and 180 μl of first reagent were mixed together and the resulting liquid mixture was left standing at 37° C. for 5 minutes. Then, 45 μl of second reagent was added to the liquid mixture to initiate reaction. All these operations were carried out automatically by setting parameters. At every 0.3 minutes after the mixing of the sample with the first reagent, absorbance (450 nm) of the liquid mixture was automatically measured.

Concentration of direct bilirubin was determined in the following manner: the first reagent and the sample were mixed together, and absorbance at 450 nm of the resulting solution mixture was measured to obtain the measurement value as "absorbance A". Then, the second reagent was added to the solution mixture to initiate oxidation reaction. Absorbance of the reaction solution was again measured to obtain the measurement value as "absorbance B". The values of absorbance A and absorbance B thus obtained were corrected for the solution volume and then a change in absorbance before and after the oxidation reaction was obtained. Concentration of direct bilirubin in the sample was determined from the change in absorbance thus obtained and a working curve prepared in advance on the basis of changes in absorbance obtained in the same manner as above, using standard solutions of known direct bilirubin concentrations.

iv) Results:

The results thus obtained are given in Table 1. As is evident from the results of Table 1, direct bilirubin can be measured much selectively with a high sensitivity by conducting the measurement in the presence of Adekatol SO-135 and Adekatol NP-720.

EXAMPLE 14

Measurement of Direct Bilirubin by Vanadic Acid Method and BOD Method Based on the Presence of Non-Ionic Surfactant i) Object:

Direct bilirubin was measured by adding to a sample Adekatol SO-135 as a non-ionic surfactant selected from polyoxyethylene (n-alkyl or iso-alkyl)ethers having an HLB value of not less than 12 but less than 15 and polyoxyethylene (n-alkylphenyl) ethers having an HLB value of 12 to 19, allowing vanadic acid or bilirubin oxidase (BOD) to act on the resulting liquid mixture, and measuring optical changes of 450 nm of the sample to prepare a working curve.

ii) Reagents used:

First Reagent:

An aqueous solution containing the following components, adjusted to pH 3.70 by NaOH, was used as a first reagent:

TABLE 1

Results of measurement of direct bilirubin in samples
(direct bilirubin, indirect bilirubin and serum) by the present method

|  | Components further contained in the first reagent | Correlation coefficient | Measurement of direct bilirubin 10 mg/dl | Measurement of direct bilirubin 50 mg/dl | Measurement of indirect bilirubin (50 mg/dl) | Measurement of serum* |
|---|---|---|---|---|---|---|
| Comp. Ex. 1 | None | 0.994 | 9.4 | 33.0 | 21.9 | 6.0 |
| Ex. 4 | 1.00% Adekatol SO-135 (HLB 13.5) | 0.998 | 11.5 | 50.0 | 14.0 | 4.8 |
| Ex. 5 | 1.00% Adekatol SO-135 and 20 mM thiourea | >0.999 | 10.7 | 49.9 | 11.7 | 4.2 |
| Ex. 6 | 1.00% Adekatol SO-135 and 20 mM hydrazinium dichloride | >0.999 | 11.2 | 50.5 | 10.1 | 4.0 |
| Ex. 7 | 1.00% Adekatol SO-135 and 1% PVP25 | >0.999 | 11.3 | 49.8 | 14.5 | 4.9 |
| Ex. 8 | 1.00% Adekatol SO-135, 20 mM thiourea and 20 mM hydrazine dichloride | >0.999 | 10.8 | 50.3 | 3.9 | 2.7 |
| Ex. 9 | 1.00% Adekatol SO-135, 20 mM thiourea and 1% PVP25 | >0.999 | 10.4 | 50.3 | 6.1 | 3.1 |
| Ex. 10 | 1.00% Adekatol SO-135 and 20 mM hydrazinium dichloride | >0.999 | 10.9 | 50.1 | 9.5 | 3.8 |
| Ex. 11 | 1.00% Adekatol SO-135, 20 mM thiourea 20 mM hydrazinium dichloride and 1% PVP25 | >0.999 | 10.4 | 49.3 | 2.4 | 2.3 |
| Comp. Ex. 2 | 20 mM thiourea, 20 mM hydrazinium dichloride and 1% PVP25 | 0.995 | 10.7 | 40.0 | 6.8 | 3.3 |
| Comp. Ex. 3 | 1.00% Triton X405, (HLB 17.9), 20 mM thiourea, 20 mM hydrazinium dichloride and 1% PVP25 | 0.998 | 10.8 | 47.6 | 2.6 | 2.5 |
| Ex. 12 | 1.00% Adekatol NP-720 (HLB 14.1), 20 mM thiourea, 20 mM hydrazinium dichloride and 1% PVP25 | >0.999 | 10.3 | 50.0 | 2.8 | 2.4 |
| Ex. 13 | 1.00% Adekatol NP-695 (HLB 13.0), 20 mM thiourea, 20 mM hyrdazinium dichloride and 1% PVP25 | >0.999 | 10.2 | 49.2 | 2.8 | 2.4 |

Serum*: containing 2.3 mg/dl of direct bilirubin and 12.1 mg/dl of total bilirubin.

| | |
|---|---|
| Citric acid monohydrate | 100 mM |
| EDTA | 1 mM |
| Adekatol SO-135 | 1.00% |

Second Reagent:

A physiological saline solution containing 3 mM of vanadic acid or a physiological saline solution containing 200 u/l of bilirubin oxidase was used as a second reagent.

Sample:

Ditaurobilirubin was used as a sample.

Figure 6:
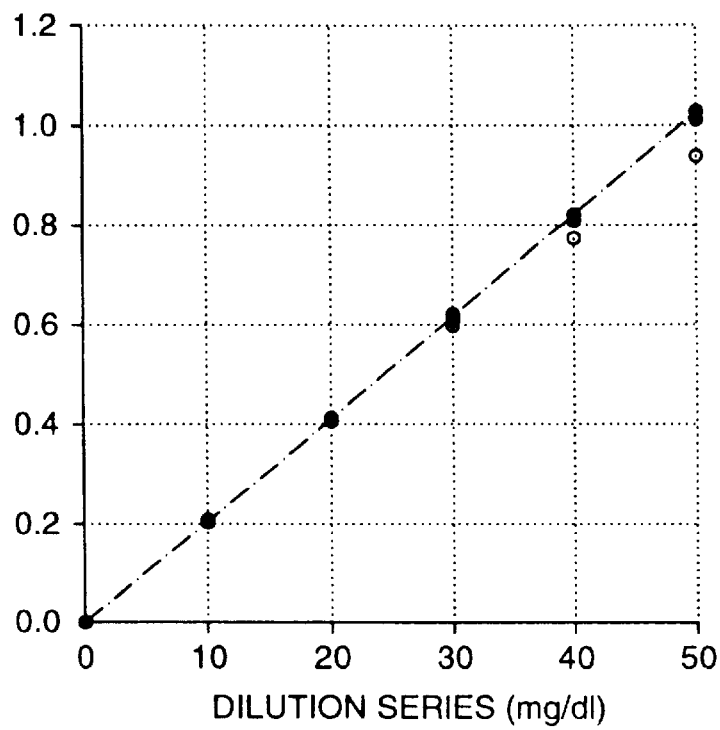
FIG. 6 shows a working curve obtained by measuring direct bilirubin by the present method for measuring direct bilirubin using vanadic acid as an oxidizing agent in the presence of a specific non-ionic surfactant.
Figure 7:
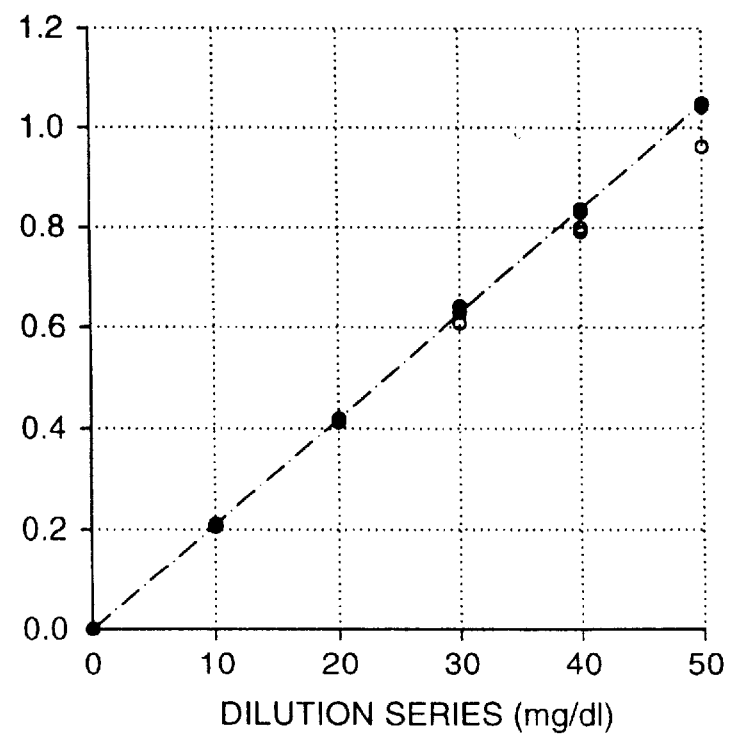
FIG. 7 shows a working curve obtained by measuring direct bilirubin by the present method for measuring direct bilirubin using bilirubin oxidase as an oxidizing agent in the presence of a specific non-ionic surfactant.

Working Curves:

Working curves were obtained by carrying out measurement according to the procedure described in Examples 5 to 13 and Comparative Examples 1 to 3, using samples containing 10 mg/dl, 20 mg/dl, 30 mg/dl, 40 mg/dl and 50 mg/dl of ditaurobilirubin, respectively.

iii) Results:

Working curves obtained by the vanadic acid method and the BOD method are shown in FIGS. 6 and 7, respectively.

The working curves shown in FIGS. 6 and 7 show a good linearity and it can be seen therefrom that direct bilirubin at a high concentration can be measured with a high sensitivity by a method for measuring direct bilirubin, using vanadic acid or BOD as an oxidizing agent in the presence of a specific non-ionic surfactant according to the present invention.

Industrial Applicability

As is evident from the foregoing, the present invention is characterized by using nitrous acid as an oxidizing agent for bilirubin, using a reaction inhibitor for indirect bilirubin in the measurement of direct bilirubin, and using a reaction accelerator in the measurement of total bilirubin. Furthermore, the present invention is characterized by measuring direct bilirubin in the presence of a specific non-ionic surfactant. The present method having such characteristics as above has a good correlation to the conventional BOD method having a distinguished precision and also reagents to be used for the measurement have a very good stability. Furthermore, the present method is applicable to measurement of bilirubin by an automatic analyzer and thus has a good contribution to measurement in clinical tests.

We claim:

1. A method for measuring total bilirubin or direct bilirubin in a body fluid sample containing bilirubin, which comprises:

adding to said fluid sample nitrous acid as an oxidizing agent to oxidize bilirubin in said sample of body fluid, and measuring optical changes of the sample.

2. A method for measuring direct bilirubin in a body fluid sample containing bilirubin, which comprises:

adding to said fluid sample nitrous acid as an oxidizing agent to oxidize bilirubin in said sample of body fluid in the presence of a reaction inhibitor capable of inhibiting oxidation of indirect bilirubin, and measuring optical changes of the sample.

3. A method for measuring total bilirubin in a body fluid sample containing bilirubin, which comprises:

adding to said fluid sample nitrous acid as an oxidizing agent to oxidize bilirubin in said sample of body fluid in the presence of a reaction accelerator capable of accelerating oxidation of indirect bilirubin, and measuring optical changes of the sample.

4. A method for measuring direct bilirubin in a body fluid sample containing bilirubin, which comprises:

adding to said fluid sample nitrous acid as an oxidizing agent to oxidize bilirubin in said sample of body fluid in the presence of at least one non-ionic surfactant selected from the group consisting of polyoxyethylene (n-alkyl or iso-alkyl)ethers having an HLB value of not less than 12 but less than 15 and polyoxyethylene (n-alkylphenyl)ethers having an HLB value of not less than 12 but not more than 19, and measuring optical changes of the sample.

5. A method according to claim 4, wherein a reaction inhibitor for inhibiting oxidation of indirect bilirubin is used together with the at least one non-ionic surfactant.

6. A method according to claim 5, wherein polyvinylpyrrolidone in addition to said reaction inhibitor is used for more selective measurement of direct bilirubin.

7. A kit for measuring direct bilirubin in a sample of living body fluid containing bilirubin, which comprises two separate reagents:

i) an acidic solution containing a least one surfactant selected from the group consisting of polyoxyethylene (n-alkyl or iso-alkyl)ethers having an HLB value of not less than 12 but less than 15 and polyoxyethylene (n-alkylphenyl)ethers having an HLB value of not less than 12 but not more than 19, and ii) a nitrite solution for oxidizing bilirubin.

8. A method for measuring direct bilirubin in a body fluid sample containing bilirubin, which comprises:

adding to said sample an oxidizing agent to react with bilirubin in said sample of body fluid in the presence of at least one non-ionic surfactant selected from the group consisting of polyoxyethylene (n-alkyl or iso-alkyl)ethers having an HLB value of not less than 12 but less than 15 and polyoxyethylene (n-alkylphenyl) ethers having an HLB value of not less than 12 but not more than 14.8, and measuring optical changes of the sample.

9. A method according to claim 8, wherein a reaction inhibitor for inhibiting oxidation of indirect bilirubin is used together with the at least one non-ionic surfactant.

10. A method according to claim 9, wherein polyvinylpyrrolidone in addition to said reaction inhibitor is used for more selective measurement of direct bilirubin.

11. A kit for measuring direct bilirubin in a sample of living body fluid containing bilirubin, which comprises two separate reagents: i) an acidic solution containing at least one non-ionic surfactant selected from the group consisting of polyoxyethylene (n-alkyl or iso-alkyl) ethers having an HLB value of not less than 12 but less than 15 and polyoxyethylene (n-alkylphenyl)ethers having an HLB value of not less than 12 but less than 14.8, and ii) an oxidizing agent solution.

* * * * *